United States Patent
Hsieh et al.

(10) Patent No.: US 10,512,588 B2
(45) Date of Patent: Dec. 24, 2019

(54) SEXUAL STIMULATING SYSTEM AND METHOD WITH FEEDBACK CONTROL

(71) Applicant: Nuworld Corporation, Hsinchu (TW)

(72) Inventors: Jung-Hsi Hsieh, Zhubei (TW);
Jia-Hua Hong, Keelung (TW);
Chun-Hsien Lin, Hsinchu (TW)

(73) Assignee: NUWORLD CORPORATION, Hsinchu (TW)

( * ) Notice: Subject to any disclaimer, the term of this patent is extended or adjusted under 35 U.S.C. 154(b) by 528 days.

(21) Appl. No.: 15/297,780

(22) Filed: Oct. 19, 2016

(65) Prior Publication Data
US 2017/0296424 A1 Oct. 19, 2017

(30) Foreign Application Priority Data
Apr. 13, 2016 (TW) ................. 105111437 A

(51) Int. Cl.
*A61H 19/00* (2006.01)

(52) U.S. Cl.
CPC ...... *A61H 19/00* (2013.01); *A61B 2562/0204* (2013.01); *A61B 2562/0219* (2013.01); *A61H 2201/501* (2013.01); *A61H 2201/5097* (2013.01); *A61H 2230/045* (2013.01); *A61H 2230/065* (2013.01); *A61H 2230/405* (2013.01); *A61H 2230/505* (2013.01); *A61H 2230/605* (2013.01); *A61H 2230/655* (2013.01)

(58) Field of Classification Search
CPC ........ A61H 19/00; A61H 19/30; A61H 19/32; A61H 19/34; A61H 19/44; A61H 19/50; A61H 23/00; A61H 2201/5025; A61H 2201/5084

USPC ...................................................... 600/38–41
See application file for complete search history.

(56) References Cited

U.S. PATENT DOCUMENTS

| | | | |
|---|---|---|---|
| 9,173,806 B1 * | 11/2015 | Dematio ................. | A61H 23/00 |
| 2016/0000642 A1 * | 1/2016 | Zipper .................... | A61H 19/34 |
| | | | 600/38 |
| 2016/0199249 A1 * | 7/2016 | Dunham ................ | A61H 19/44 |
| | | | 601/15 |

FOREIGN PATENT DOCUMENTS

| TW | 200938278 A | 9/2009 |
| TW | I370732 B | 8/2012 |
| TW | 201611775 A | 4/2016 |

OTHER PUBLICATIONS

Search Report issued in counterpart Taiwanese application No. 105111437 dated Nov. 28, 2016, and corresponding English translation.

\* cited by examiner

*Primary Examiner* — Samuel G Gilbert
(74) *Attorney, Agent, or Firm* — Hamre, Schumann, Mueller & Larson, P.C.

(57) ABSTRACT

A sexual stimulating system with feedback control includes a physiological sensor, a sexual stimulator, and a processing module. The physiological sensor measures a physiological response of a user under sexual stimulation, and generates a sensor signal according to a result of the measurement of the physiological response. The sexual stimulator applies the sexual stimulation. The processing module is electrically connected to the physiological sensor and the sexual stimulator, receives the sensor signal, performs an analytical procedure upon the sensor signal for generating digital data, and generates a driving signal according to the digital data to control a degree of the sexual stimulation.

11 Claims, 5 Drawing Sheets

SEXUAL STIMULATING SYSTEM AND METHOD WITH FEEDBACK CONTROL

CROSS-REFERENCE TO RELATED APPLICATION

This application claims priority of Taiwanese Patent Application No. 105111437, filed on Apr. 13, 2016.

FIELD

The disclosure relates to feedback control, and more particularly to a sexual stimulating system with feedback control and a sexual simulating method with feedback control which are able to prevent excessive sexual stimulation based on user's physiological responses.

BACKGROUND

For a conventional sexual stimulation device, a degree of sexual stimulation applied thereby is manually controlled, which is less than ideal. A patient with hypertension or cardiac disease cannot afford intense sexual stimulation and needs a way of prevention from risk of excessive stimulation. In addition, a disabled person with reduced mobility or reduced ability of expression may need an approach to automatically adjust the degree of sexual stimulation based on physiological responses in replace of the conventional manual operation.

SUMMARY

Therefore, an object of the disclosure is to provide a sexual stimulating system and method with feedback control that can alleviate at least one of the drawbacks of the prior art.

According to a first aspect of the disclosure, the sexual stimulating system with feedback control includes a physiological sensor, a sexual stimulator and a processing module.

The physiological sensor is configured to measure a physiological response of a user under sexual stimulation, and to generate a sensor signal according to a result of the measurement of the physiological response.

The sexual stimulator is configured to apply the sexual stimulation.

The processing module is electrically connected to the physiological sensor and the sexual stimulator. The processing module is configured to receive the sensor signal generated by the physiological sensor, to perform an analytical procedure upon the sensor signal for generating digital data, and to generate a driving signal according to the digital data to control a degree of the sexual stimulation applied by the sexual stimulator.

According to a second aspect of the disclosure, the sexual stimulating method with feedback control is implemented by a sexual stimulating system, which includes a physiological sensor, a sexual stimulator and a processing module. The sexual stimulating method includes the steps of:

a) by the physiological sensor, measuring a physiological response of a user under sexual stimulation, and generating a sensor signal according to a result of the measurement of the physiological response;

b) generating, by the processing module after obtaining the sensor signal, digital data by performing an analytical procedure upon the sensor signal; and c) generating, by the processing module, a driving signal according to the digital data to control a degree of the sexual stimulation applied by the sexual stimulator.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
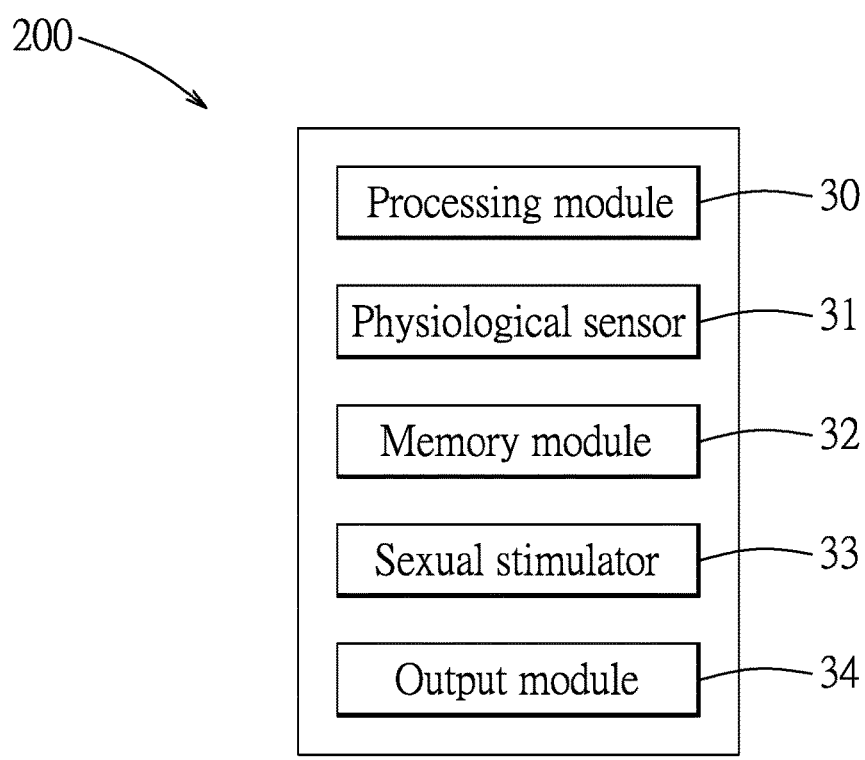
FIG. 1 is a block diagram illustrating a first embodiment of a sexual stimulating system with feedback control according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, a first embodiment of a sexual stimulating system 200 according to the disclosure is illustrated. The sexual stimulating system 200 may be a sex toy and may be worn on an erogenous zone of a user. The first embodiment of the sexual stimulating system 200 includes a physiological sensor 31, a memory module 32, a sexual stimulator 33, an output module 34, and a processing module 30 electrically connected to the physiological sensor 31, the memory module 32, the sexual stimulator 33 and the output module 34.

The physiological sensor 31 is configured to measure a physiological response of a user under sexual stimulation, and to generate a sensor signal according to a result of the measurement of the physiological response.

Figure 2:
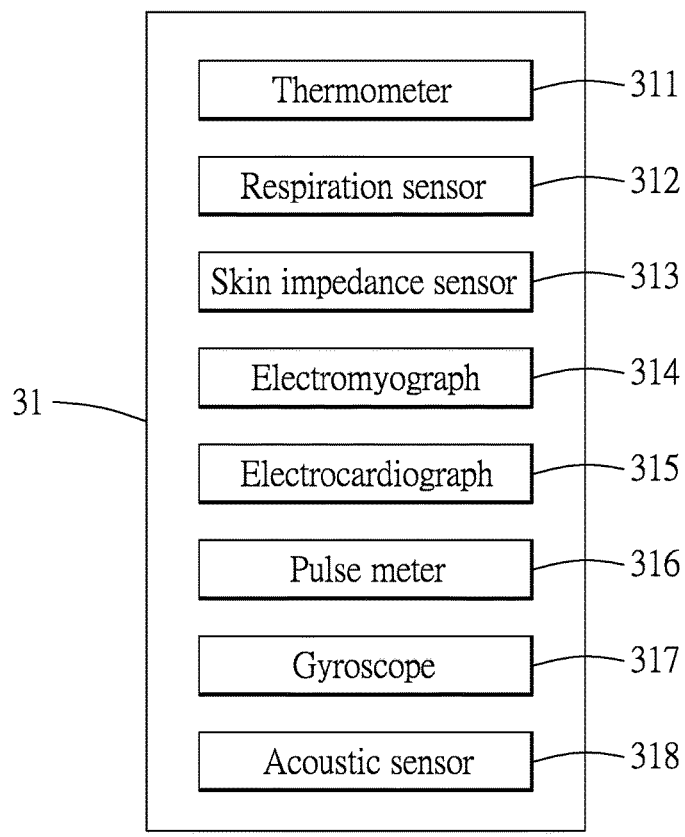
FIG. 2 is a block diagram illustrating one example of a physiological sensor of the first embodiment.

Referring to FIG. 2, the physiological sensor 31 may be selected from the group consisting of a thermometer 311, a respiration sensor 312, a skin impedance sensor 313, an electromyograph 314, an electrocardiograph 315, a pulse meter 316, a gyroscope 317, an acoustic sensor 318 and combinations thereof. In this embodiment, the physiological sensor 31 includes all of the above-listed components 311-318.

The thermometer 311 generates a thermal signal according to a result of measurement of body temperature of the user. The respiration sensor 312 generates a respiration signal according to a result of measurement of a respiration rate of the user. The skin impedance sensor 313 generates an impedance signal according to a result of measurement of skin impedance of the user. The electromyograph 314 generates an EMG (electromyogram) signal according to a result of measurement of electrical activity produced by skeletal muscles of the user. The electrocardiograph 315 generates an ECG (electrocardiogram) signal according to a result of measurement of electrical activity of heart of the user. The pulse meter 316 generates a pulse signal according to a pulse of the user. The pulse signal may, for instance, indicate a pulse rate of the user in some embodiments. The gyroscope 317 generates an acceleration signal according to a result of measurement of acceleration of a measured part of the user. The acoustic sensor 318 generates an acoustic signal according to a result of measurement of frequency and/or amplitude of sound made by the user. The thermal signal, the respiration signal, the impedance signal, the EMG signal, the EGG signal, the pulsation signal, the acceleration signal, and the acoustic signal serve as the sensor signal mentioned above and are transmitted to the processing module 30.

The memory module 32 is configured to store predetermined reference data which are established in advance and which are associated with a normal physiological response under normal sexual stimulation. The predetermined reference data associated with the normal physiological response may be established in factory according to statistics based on experiment results of general users under normal sexual stimulation, or may be established according to physiological response of the user under sexual stimulation when under appropriate, normal sexual stimulation using the sexual stimulating system 200 of the disclosure during initial setup of the sexual stimulating system 200. The normal physiological response may be exemplified as at least one of a body temperature curve, the respiration rate, skin impedance variation, an EMG, an ECG, pulse rate variation, the acceleration of the measured part, or variation in the sound made by the user.

The sexual stimulator 33 is configured to apply sexual stimulation. The sexual stimulator 33 may be, but is not limited to, a vibrator configured to vibrate for applying the sexual stimulation.

The processing module 30 is configured to receive the sensor signal generated by the physiological sensor 31, to perform an analytical procedure upon the sensor signal for generating digital data, and to generate a driving signal according to the digital data to control a degree of the sexual stimulation applied by the sexual stimulator 33. For example, the processing module 30 generates the digital data to adjust at least one of a frequency, an amplitude or a duration of vibration of the vibrator for adjusting the degree of the sexual stimulation.

The analytical procedure mentioned above may include, but is not limited to, a time-domain analysis step, an averaging step, a frequency-domain analysis step, and/or an energy calculation step. Performance of the time-domain analysis step results in the digital data of the sensor signal being in time domain. Performance of the frequency-domain analysis step results in the digital data of the sensor signal being in frequency domain. Performance of the averaging step results in the digital data indicating an average of the sensor signal. Performance of the energy calculation step results in the digital data indicating energy of the sensor signal.

Moreover, the processing module is further configured to compare the digital data with the predetermined reference data so as to determine whether the user's physiological condition is in an abnormal state and whether to reduce the degree of the sexual stimulation applied by the sexual stimulator 33, e.g., to reduce at least one of the frequency, the amplitude or the duration of vibration of the vibrator. Besides controlling the sexual stimulator 33 to reduce the degree of the sexual stimulation, the processing module 30 is further configured to control the output module 34 to output a warning signal when the processing module 30 determines that the user's physiological condition is in the abnormal state based on a result of comparison between the digital data and the predetermined reference data. The output module 34 herein may for instance be a monitor or a speaker.

Figure 3:
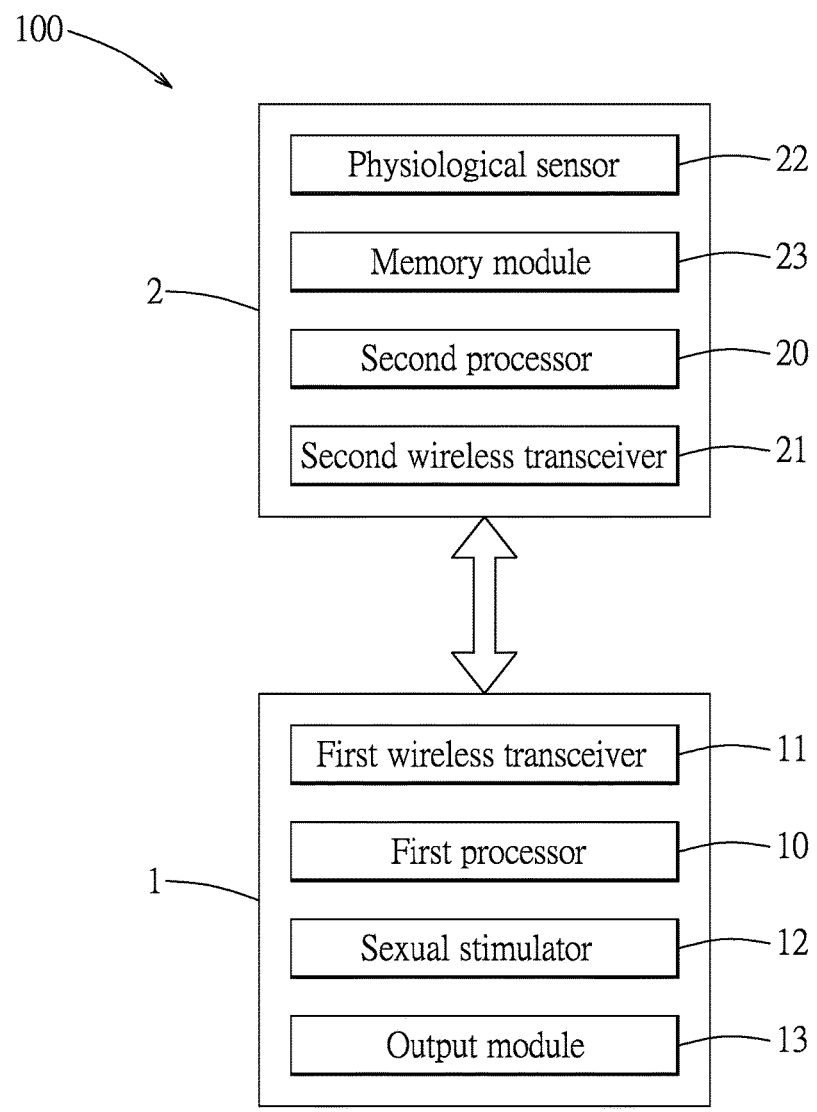
FIG. 3 is a block diagram illustrating a second embodiment of the sexual stimulating system with feedback control according to the disclosure.

Referring to FIG. 3, a second embodiment of the sexual stimulating system 100 according to the disclosure is illustrated. The second embodiment is similar to the first embodiment. However, the sexual stimulating system 100 includes a first device 1, and a second device 2 physically separated from the first device 1. The first device 1 may be a sex toy and may be worn on the erogenous zone of the user.

The first device 1 includes a first wireless transceiver 11, the sexual stimulator 12, the output module 13, and a first processor 10 electrically connected to and controlling operations of the first wireless transceiver 11, the sexual stimulator 12, and the output module 13.

The second device 2 includes a second wireless transceiver 21, the physiological sensor 22, the memory module 23, and a second processor 20 electrically connected to and controlling operations of the second wireless transceiver 21, the physiological sensor 22, and the memory module 23. The second processor 20 in combination with the first processor 10 may serve as the processing module 30 of the first embodiment (see FIG. 1).

The second processor 20 is configured to receive the sensor signal generated by the physiological sensor 22, to perform the analytical procedure upon the sensor signal for generating the digital data, and to send the digital data via the second wireless transceiver 21 to the first wireless transceiver 11 of the first device 1. The physiological sensor 22 and the analytical procedure are similar to those discussed in the first embodiment, and description thereof will be omitted.

It is noted that after the first and second device 1 and 2 are booted, the first and second wireless transceivers 11 and 21 will automatically establish a wireless communication channel therebetween by a pairing process for preventing interference from other devices. In this embodiment, the first and second wireless transceivers 11 and 21 may be short-range wireless communication modules like Bluetooth modules.

The first processor 10 is configured to receive the digital data via the first wireless transceiver 11, and to generate the driving signal according to the digital data. The sexual stimulator 12 may be, but is not limited to, a vibrator configured to vibrate for applying the sexual stimulation on the erogenous zone of the user. The frequency, the amplitude and the duration of vibration of the vibrator are controlled according to the driving signal generated by the first processor 10, to control the degree of the sexual stimulation.

Moreover, the memory module 23 is configured to store predetermined reference data associated with the normal physiological response. Since the predetermined reference data are similar to the predetermined reference data stored in the memory module 32 of the first embodiment, detailed descriptions of the same are omitted herein for the sake of brevity.

The second processor 20 is further configured to compare the digital data wish the predetermined reference data so as to determine whether the user's physiological condition is in the abnormal state and whether or not to notify the first processor 10 to reduce the degree of the sexual stimulation applied by the sexual stimulator 12, e.g., to reduce at least one of the frequency, the amplitude or the duration of vibration of the vibrator. Additionally, the second processor 20 is further configured to notify, via the second wireless transceiver 21 and the first wireless transceiver 11, the first processor 10 to control the output module 13 to output the warning signal when the second processor 20 determines that the user's physiological condition is in the abnormal state based on the result of comparison between the digital data and the predetermined reference data.

Figure 4:
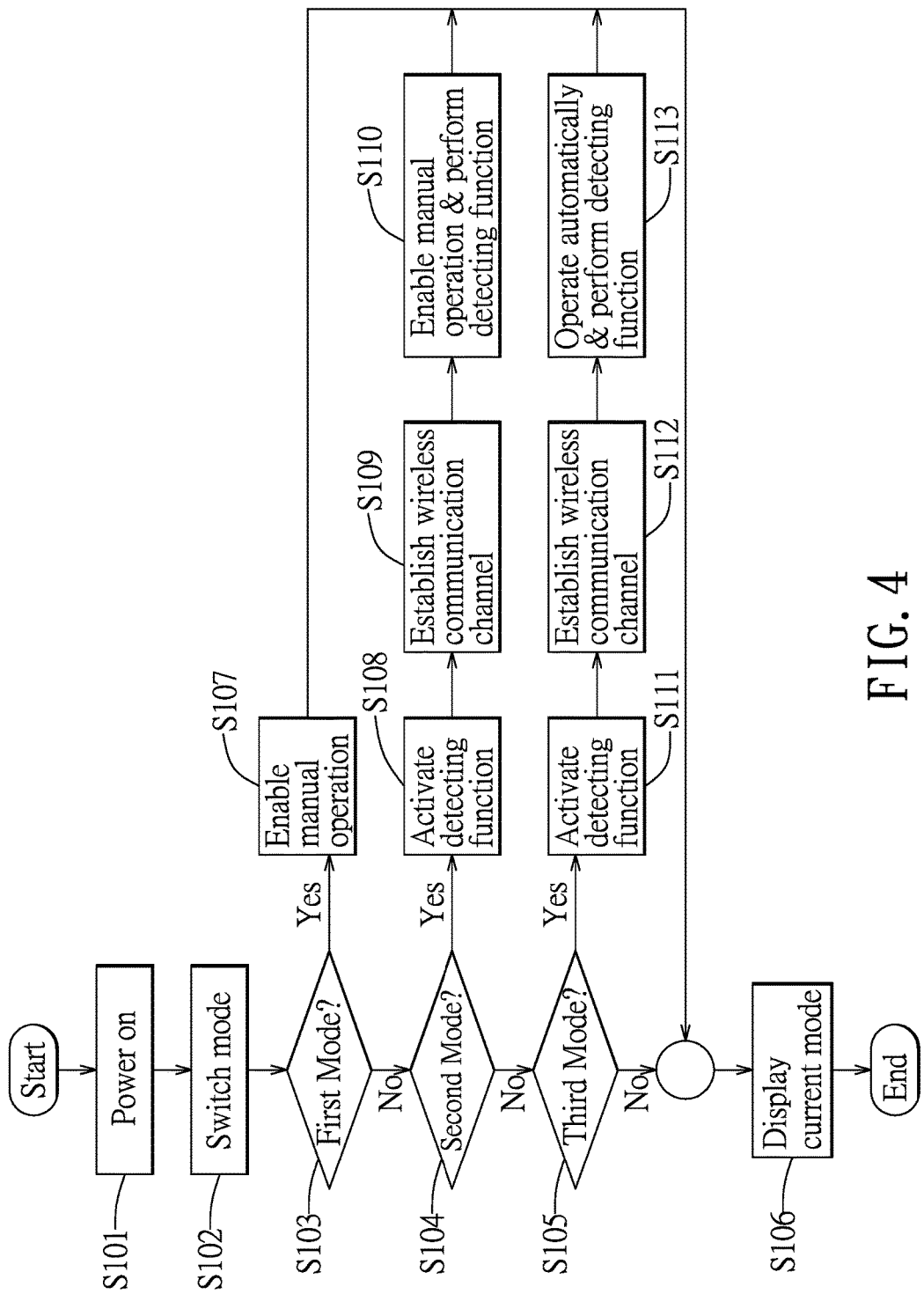
FIG. 4 is a flow chart illustrating an operation flow of the second embodiment of the sexual stimulating system with feedback control.

Referring to FIG. 4 in combination with FIG. 3, an operation flow of the second embodiment of the sexual stimulating system 100 which is operable to switch between different operating modes is illustrated. In step S101, the sexual stimulating system 100 is powered on. In step S102, the sexual stimulating system 100 is operated by the user to switch between three operating modes, i.e., a first mode (S103), a second mode (S104) and a third mode (S103). Moreover, in step S106, the first device 1 is configured to display a current one of the operating modes by means of the output module 13.

In the first mode, manual operation of the first device 1 is enabled, i.e., the degree of the sexual stimulation applied by the sexual stimulator 12 is adjustable manually by the user (step S107).

In the second mode, the second device 2 activates a detecting function (step S108). The detecting function enables the second processor 20 to determine whether the user's physiological condition is in the abnormal state based on the result of comparison between the digital data and the predetermined reference data. The first and second devices 1 and 2 are paired up to establish the wireless communication channel therebetween (step S109). Manual operation of the first device 1 is enabled and the second device 2 performs the detecting function (step S110).

In the third mode, similar to steps S108 and S109 in the second mode, the second device 2 activates the detecting function (S111), and the first and second devices 1 and 2 are paired up to establish the wireless communication channel therebetween (step S112). However, the first device 1 is operated automatically, i.e., the degree of the sexual stimulation is controlled automatically according to the physiological response of the user, and the second device 2 performs the detecting function (step S113).

By omitting steps S109 and S112 of establishing the wireless communication channel, the operation flow shown in FIG. 4 is applicable to the sexual stimulating system 200 in the first embodiment.

Figure 5:
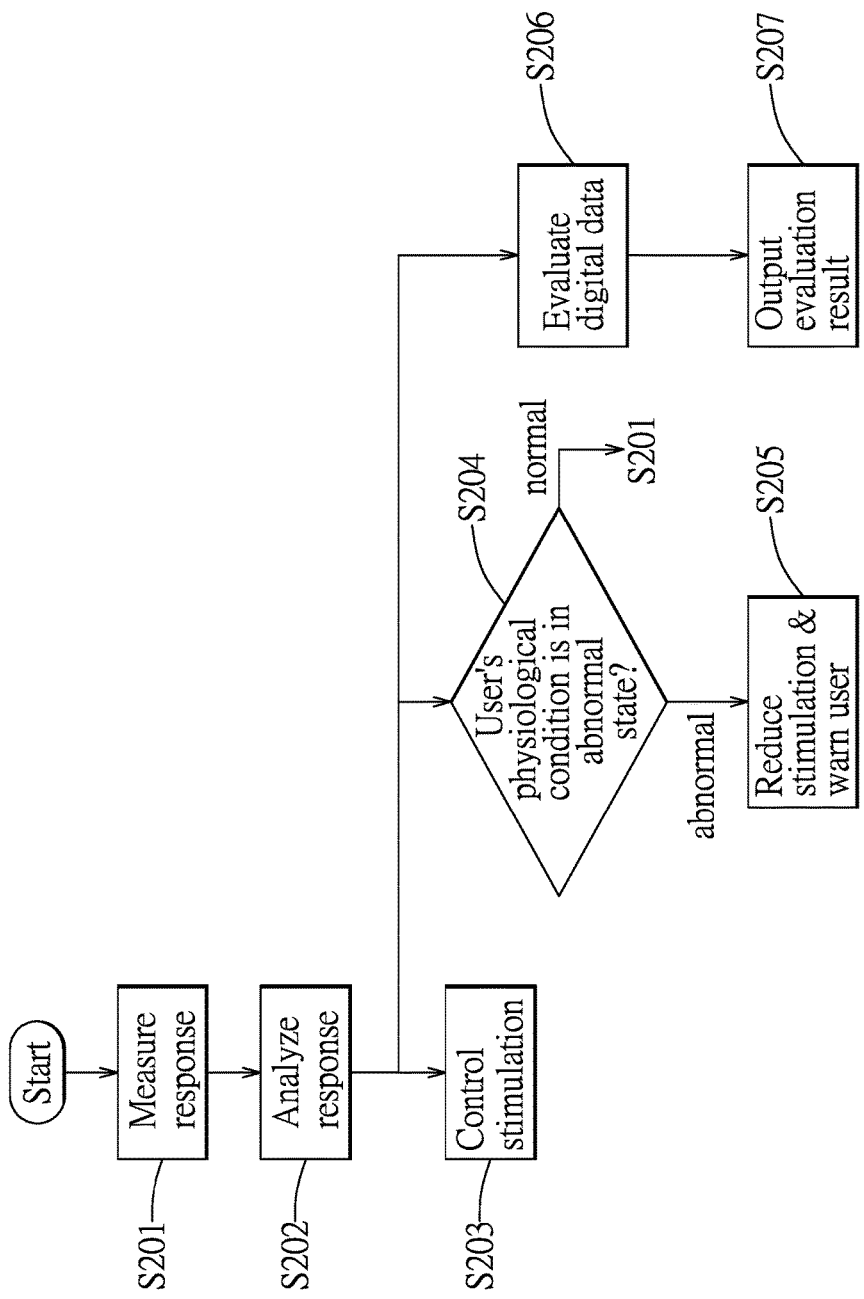
FIG. 5 is a flow chart illustrating an embodiment of a sexual stimulating method with feedback control according to the disclosure.

Referring to FIG. 5 in combination with FIG. 3, a sexual stimulating method with feedback control according to the disclosure is illustrated. The sexual stimulating method is to be implemented by the sexual stimulating system 100 which is operating in the third mode shown in FIG. 4. Moreover, the first device 1 is placed on the erogenous zone of the user for applying the sexual stimulation, and the second device 2 is placed on a body part of the user where the physiological response can be conveniently measured. The ECG signal will be used to exemplify the sensor signal for explanation of the sexual stimulating method, but it is noted that the sexual stimulating method is suitable for other types of sensor signals as well. Furthermore, the sexual stimulator is exemplified by the vibrator. The sexual stimulating method includes the following steps S201 to S207 which are performed after the sexual stimulating system 100 is powered on and the sexual stimulator 12 is activated to apply the sexual stimulation.

In step S201, the physiological sensor 22 measures the physiological response of the user under the sexual stimulation, generates the sensor signal according to the result of the measurement of the physiological response, and sends the sensor signal to the second processor 20. For example, the ECG signal is measured which corresponds to the electrical activity of heart of the user under the sexual stimulation.

In step S202, after obtaining the sensor signal, the second processor 20 generates the digital data by performing the analytical procedure, e.g., the time-domain analysis step, the averaging step, the frequency-domain analysis step and/or the energy calculation step, upon the sensor signal, and sends the digital data to the first processor 10 via the first and second wireless transceivers 11 and 21.

In step S203, the first processor 10 generates the driving signal according to the digital data, and transmits the driving signal to the sexual stimulator 12 to control the degree of the sexual stimulation applied thereby, e.g., to adjust at least one of the frequency, the amplitude or the duration of vibration of the vibrator. It should be noted that steps S201 and S203 correspond to the aforementioned automatic operation of the first device 1 (see step S113) of FIG. 4.

Meanwhile, in step S204, the second processor 20 compares the digital data thus generated with the predetermined reference data stored in the memory module 23 so as to determine whether the user's physiological condition is in the abnormal state so as to decide whether to reduce the degree of the sexual stimulation applied by the sexual stimulator 12.

In step S205, when it is determined by the second processor 20 that the user's physiological condition is in the abnormal state, the second processor 20 notifies, via the second and first wireless transceivers 21 and 11, the first processor 10 to reduce the degree of the sexual stimulation and to output the warning signal by the output module 13. Specifically, the first processor 10 controls the vibrator to stop vibrating when the ECG signal which corresponds to the electrical activity of the heart of the user is determined as abnormal by the second processor 20. It should be noted that steps S204 and S205 correspond to the aforementioned detecting function of FIG. 4.

Furthermore, in step S206, the second processor 20 evaluates the digital data according to an evaluation standard, which classifies the digital data into different groups representing different sexual arousal states of the user, to obtain an evaluation result. The sexual arousal states may include, but are not limited to, excitement, normality and frustration states.

In step S207, the second processor 20 notifies, via the first and second wireless transceivers 11 and 21, the first processor 10 to control the output module 13 to output the evaluation result which indicates one the sexual arousal states corresponding to the group into which the digital data is classified.

For example, the evaluation standard may classify the digital data which corresponds to the ECG signal into one of the groups representing the excitement state corresponding to a higher rate of change of heart rate, the normality state corresponding to substantially no rate of change of heart rate, or the frustration state corresponding to a smaller rate of change of heart rate. The evaluation result which indicates one of the sexual arousal states is then outputted by the output module 13. The evaluation standard may vary depending on different sensor signals obtained respectively by the thermometer 311, the respiration sensor 312, the skin impedance sensor 313, the electromyograph 314, the electrocardiograph 315, the pulse meter 316, the gyroscope 317, the acoustic sensor 318 and combinations thereof. However, analogous principle is applicable to different evaluation standards.

This disclosure achieves functions described in the following. By measuring continuously via the physiological sensor 31 the physiological response of the user under sexual stimulation, the processing module 30 (FIG. 1), or the combination of the first and second processors 10, 20 (FIG. 3), is able to generate the driving signal correspondingly to implement automatic operation of the sexual stimulator 33 (FIG. 1), 12 (FIG. 3), and is further able to determine whether the user's physiological condition is in an abnormal state and whether to reduce the degree of the sexual stimulation applied by the sexual stimulator 33, 12. When it is determined that the user's physiological condition is in the abnormal state, the processing module 30 (or the processors 10 and 20 combined) reduces the degree of the sexual stimulation, and the output module 34, 13 outputs the warning signal. Therefore, risk of excessive stimulation is prevented. Moreover, the sexual arousal states, such as excitement, normality and frustration states of the user, may be determined by the processing module 30 (or the processors 10 and 20 combined) through evaluation, and the evaluation result will be outputted by the output module 34, 13.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A sexual stimulating system with feedback control comprising:
   a physiological sensor configured to measure a physiological response of a user under sexual stimulation, and to generate a sensor signal according to a result of the measurement of the physiological response;
   a sexual stimulator configured to apply the sexual stimulation;
   a processing module electrically connected to said physiological sensor and said sexual stimulator, said processing module configured to receive the sensor signal generated by said physiological sensor, to perform an analytical procedure upon the sensor signal for generating digital data, and to generate a driving signal according to the digital data to control a degree of the sexual stimulation applied by the sexual stimulator;
   a memory module which is electrically connected to said processing module and is configured to store predetermined reference data associated with a normal physiological response; and
   an output module electrically connected to said processing module, said output module configured to be controlled by said processing module to output a warning signal when said processing module determines that a user's physiological condition is in an abnormal state based on a result of comparison between the digital data and the predetermined reference data,
   wherein said processing module is further configured to compare the digital data with the predetermined reference data so as to determine whether to reduce the degree of the sexual stimulation applied by said sexual stimulator.

2. The sexual stimulating system as claimed in claim 1, wherein said processing module is further configured to control said sexual stimulator to reduce the degree of the sexual stimulation when said processing module determines that the user's physiological condition is in the abnormal state.

3. The sexual stimulating system as claimed in claim 1, wherein said sexual stimulator is a vibrator configured to vibrate for applying the sexual stimulation, and said processing module generates the driving signal to adjust at least one of a frequency, an amplitude or a duration of vibration of said vibrator for controlling the degree of the sexual stimulation.

4. The sexual stimulating system as claimed in claim 1, wherein said physiological sensor is selected from the group consisting of a thermometer, a respiration sensor, a skin impedance sensor, an electromyograph, an electrocardiograph, a pulse meter, a gyroscope, an acoustic sensor and combinations thereof.

5. The sexual stimulating system as claimed in claim 1, wherein the analytical procedure includes at least one of a time-domain analysis step, an averaging step, a frequency-domain analysis step, or an energy calculation step.

6. The sexual stimulating system as claimed in claim 1, being a sex toy.

7. A sexual stimulating system with feedback control comprising:
   a physiological sensor configured to measure a physiological response of a user under sexual stimulation, and to generate a sensor signal according to a result of the measurement of the physiological response;
   a sexual stimulator configured to apply the sexual stimulation;
   a processing module electrically connected to said physiological sensor and said sexual stimulator, said processing module configured to receive the sensor signal generated by said physiological sensor, to perform an analytical procedure upon the sensor signal for generating digital data, and to generate a driving signal according to the digital data to control a degree of the sexual stimulation applied by the sexual stimulator;
   a memory module which is electrically connected to said processing module and is configured to store predetermined reference data associated with a normal physiological response; and
   a first device, and a second device physically separated from said first device,
   wherein said processing module is further configured to compare the digital data with the predetermined reference data so as to determine whether to reduce the degree of the sexual stimulation applied by said sexual stimulator, and
   wherein:
   said first device includes said sexual stimulator, a first processor electrically connected to said sexual stimulator, and a first wireless transceiver electrically connected to said first processor;

said second device includes said physiological sensor, said memory module, a second processor electrically connected to said physiological sensor and said memory module, and a second wireless transceiver electrically connected to said second processor, said second processor in combination with said first processor serving as said processing module;

said second processor is configured to receive the sensor signal generated by said physiological sensor, to perform the analytical procedure upon the sensor signal for generating the digital data, and to send the digital data via said second wireless transceiver to said first wireless transceiver;

said first processor is configured to receive the digital data, and to generate the driving signal according to the digital data; and said second processor is further configured to compare the digital data with the predetermined reference data so as to determine whether or not to notify said first processor to reduce the degree of the sexual stimulation applied by said sexual stimulator.

8. A sexual stimulating method with feedback control to be implemented by a sexual stimulating system, the sexual stimulating system including a physiological sensor, a sexual stimulator and a processing module, said sexual stimulating method comprising the steps of:
   a) by the physiological sensor, measuring a physiological response of a user under sexual stimulation, and generating a sensor signal according to a result of the measurement of the physiological response;
   b) generating, by the processing module after obtaining the sensor signal, digital data by performing an analytical procedure upon the sensor signal; and
   c) generating, by the processing module, a driving signal according to the digital data to control a degree of the sexual stimulation applied by the sexual stimulator, wherein the sexual stimulating system further including an output module, the sexual stimulating method further comprising the steps of:
   a) evaluating, by the processing module, the digital data according to an evaluation standard, which classifies the digital data into different groups representing different sexual arousal states of the user, to obtain an evaluation result and
   b) outputting, by the output module, the evaluation result which indicates one the sexual arousal states.

9. The sexual stimulating method as claimed in claim 8, the sexual stimulating system further including a memory module that stores predetermined reference data associated with a normal physiological response, the sexual stimulating method further comprising the step of:
   d) comparing, by the processing module, the digital data with the predetermined reference data so as to determine whether to reduce the degree of the sexual stimulation applied by the sexual stimulator.

10. The sexual stimulating method as claimed in claim 8, the sexual stimulator being a vibrator, wherein step c) includes generating the driving signal according to the digital data to adjust at least one of a frequency, an amplitude or a duration of vibration of the vibrator for controlling the degree of the sexual stimulation.

11. The sexual stimulating method of claim 8, wherein in step b), the analytical procedure includes at least one of a time-domain analysis step, an averaging step, a frequency-domain analysis step, or an energy calculation step.

* * * * *